US00PP19857P2

(12) United States Plant Patent
van Kleinwee et al.

(10) Patent No.: US PP19,857 P2
(45) Date of Patent: Mar. 24, 2009

(54) ***ARGYRANTHEMUM FRUTESCENS* PLANT NAMED 'ARGYMIP'**

(50) Latin Name: *Argyranthemum frutescens*
Varietal Denomination: Argymip

(75) Inventors: Theodorus Cornelis Maria van Kleinwee, Hoorn (NL); Anna M. W. P. Houbraken, Fijnaart (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 12/070,002

(22) Filed: Feb. 14, 2008

(51) Int. Cl.
*A01H 5/00* (2006.01)

(52) U.S. Cl. ..... Plt./406
(58) Field of Classification Search ..... Plt./406, Plt./263
See application file for complete search history.

*Primary Examiner*—Annette H Para
*Assistant Examiner*—S. B. McCormick Ewoldt
(74) *Attorney, Agent, or Firm*—S. Matthew Edwards

(57) ABSTRACT

A new and distinct cultivar of *Argyranthemum frustescens* plant named 'Argymip' characterized by its compact plant habit with short internodes, its early, rich and long flowering and its pink flowers with contrasting dark center. The pink color is hardly fading during summer.

1 Drawing Sheet

Latin name of the genus and species of the plant claimed: *Argyranthemum frutescens.*
Varietal denomination: 'Argymip'.

BACKGROUND OF THE NEW PLANT

The present invention relates to a new and distinct cultivar of Marguerite Daisy plant, botanically known as *Argyranthemum frutescens* and hereinafter referred to by the cultivar name 'Argymip.'

The new cultivar is a product of a planned breeding program conducted in Enkhuizen, Netherlands. The new cultivar 'Argymip' has a very compact plant habit and pink flowers with a contrasting dark center.

The new *Argyranthemum* originated from an open pollination conducted in Enkhuizen, Netherlands in 2003 of a proprietary selection of *Argyranthemum frutescens* identified as code number 'G0132-1,' not patented, as the female, or seed, parent with pollen of unknown *Argyranthemum frutescens* plants as the male, or pollen, parent.

The cultivar 'Argymip' was discovered and selected as a single plant within the progeny of the stated open pollination in a controlled environment in Enkhuizen, Netherlands in August 2004. Asexual reproduction of the new *Argyranthemum* by terminal cuttings in a controlled environment in Enkhuizen, Netherlands since August 2004, has shown that the unique features of this new *Argyranthemum* are stable and reproduced true to type in successive generations.

SUMMARY OF THE INVENTION

The new *Argyranthemum* has not been observed under all possible environmental conditions. The phenotype may vary somewhat with variations in environment such as temperature and light intensity without, however, any variance in genotype.

The following characteristics have been repeatedly observed and are determined to be basic characteristics of 'Argymip' and distinguish to new *Argyranthemum* as a new and distinct cultivar:

1. Compact plant habit
2. Freely branching habit and short internodes; dense and bushy plant habit
3. Early flowering habit
4. Freely flowering habit with numerous inflorescences per plant
5. Pink coloured flowers with dark center. The pink color is hardly fading during summer.

Plants of the new *Argyranthemum* differ from plants of the female parent in the following characteristics:

1. Plants of the new *Argyranthemum* are more branched than plants of the female parent.
2. Plants of the new *Argyranthemum* flower earlier than plants of the female parent.

The difference of plants of the new *Argyranthemum* from plants of the male parent is unknown, as the male parent is unknown.

TABLE 1

DIFFERENCES BETWEEN THE NEW CULTIVAR 'ARGYMIP' AND TWO SIMILAR CULTIVARS

| | 'ARGYMIP' | 'Daisy Crazy Cherry Love' (Not patented) | 'Comet pink' (Not patented) |
|---|---|---|---|
| Plant height | 18 cm | 24 cm | 22 cm |
| Flower diameter | 3-3.5 cm | 3.5-4 cm | 3-3.5 cm |
| Foliage color | 137B | 137A | 144A |
| Disc floret color | 185A | 179A | 21A |
| Peduncle length | 5-6 cm | 6-9 cm | 5-6 cm |

DESCRIPTION OF THE PHOTOGRAPHS

The accompanying color photographs illustrate the overall appearance of the new cultivar, showing the colors as true as it is reasonably possible to obtain in colored reproductions of this type. Colors in the photograph may differ slightly from the color values cited in the detailed botanical description which accurately describe the colors of the new *Argyranthemum.*

BOTANICAL DESCRIPTION OF THE PLANT

The aforementioned photographs, the following detailed observations and averaged measurements describe plants of this new Marguerite Daisy plant. The data were collected from plants from asexual reproductions carried out in Enkhuizen, The Netherlands. The plant history was taken on 20 week old plants grown in the open field in Enkhuizen, Netherlands with day temperatures ranging from 12 to 25° C., and night temperatures ranging from 10 to 20° C.

Color references are primarily to the R.H.S. Colour Chart of The Royal Horticultural Society, 1995 Edition, except where general terms of ordinary dictionary significance are used.

The plant: Classification—Botanical: *Argyranthemum frutescens.*

Parentage:

*Female parent.*—Proprietary selection of *Argyranthemum frutescens,* identified as number 'G0132-1' (Not patented).

*Male parent.*—Unidentified plants of *Argyranthemum frutescens.*

Propagation:

*Type of cuttings.*—Terminal cuttings.

*Time to intiate roots.*—7–10 days at air temperature of 21° C.

*Time to develop roots.*—7–14 days at air temperature of 18° C.

*Root description.*—Fibrous, relatively fine, white in color.

*Rooting description.*—Freely branching, dense.

Plant description:

*Growth habit.*—Compact; rounded shape.

*Plant height.*—About 20 cm.

*Vigor.*—Weak vigor.

*Spreading area of plant.*—About 30 cm.

*Strength.*—Strong.

*Branching character.*—Freely branching, plants do not require pinching.

*Crop time.*—About 9 weeks are required to produce a finished flowering plant in a 10.5 cm container from a well developed cutting.

Lateral branch description:

*Length.*—13 cm.

*Diameter.*—2–3 mm.

*Shape.*—Round, slightly grooved.

*Anthocyanin pigmentation.*—Absent.

*Texture.*—Smooth, glabrous.

*Length of internode.*—1–2 cm.

*Pubescence.*—Absent.

*Color.*—144A.

The foliage:

*Arrangement.*—Alternate, simple.

*Shape of leaf.*—Bipinnatisect.

*Leaf apex.*—Broadly acute.

*Leaf base.*—Attenuate, clasping.

*Margin.*—Deeply dissected, laciniate.

*Texture.*—Thick glabrous smooth.

*Length.*—4–5 cm.

*Width.*—1–2 cm.

*Depth of incision.*—Laciniate.

*Color.*—Upper side: 137B; old leaf 147B. Lower side: 137C; old leaf 147B.

*Pubescence.*—Absent.

*Petiole.*—Length: About 1–2 cm. Diameter: About 2 mm. Texture: Smooth, glabrous. Color 137B.

*Venation.*—Shape: Pinnate. Color: 137C.

The inflorescence:

*Appearance.*—Daisy-type inflorescences with ligulate ray florets. Disc and ray florets develop acropetally on a capitulum. Inflorescences held upright and outwardly on terminal and axillary peduncles. Inflorescences positioned perpendicular to the peduncles. Inflorescences persistent.

*Flowering response.*—Under natural conditions, plant flower from spring to early fall; plants flower continuously during this period.

*Inflorescence longevity.*—10 days.

*Quantity of inflorescences.*—Freely flowering, about 400 open inflorescences and inflorescence buds per plant.

The flower bud:

*Peduncle.*—Length: 5–6 cm. Diameter 1–2 mm. Strength: Strong. Aspect: Upright to slightly outward. Texture: Smooth, glabrous. Color: 146B.

*Inflorescence bud.*—Height: 5 mm. Diameter: 5 mm. Shape: Ovoid. Color: N200A.

The inflorescence:

*Size.*—Diameter: 3–3.5 cm. Depth: About 6 mm.

*Disc diameter.*—About 0.9–1.1 cm.

*Flower type.*—Semi double flowered.

*Receptacle.*—Height: About 6 mm. Diameter: About 10 mm.

*Bracts.*—Number of bracts: 3 series of 5 bracts, tightly to receptacle. Shape: Elliptic. Apex: Broad. Base: Truncate. Texture: Smooth, glabrous. Margin: Entire. Length: 2–3 mm. Width: 1 mm. Color upper side: N144C. Color lower side: N138A.

*Fragrance.*—Absent.

Ray florets:

*Quantity per inflorescene.*—20, arranged in three whorls.

*Shape.*—Ligulate.

*Apex.*—Emarginate.

*Base.*—Attenuate.

*Margin.*—Entire.

*Color upper surface.*—75A.

*Color lower surface.*—N74C.

*Length.*—1.5 cm.

*Width.*—0.6–0.7 cm.

*Texture.*—Smooth, glabrous; longitudinally ridged.

Disc florets:

*Arrangement.*—Massed at the center of the inflorescence.

*Shape.*—Tubular, elongated, five-pointed; fused at base.

*Color.*—Immature: 185A. Mature: 17A.

*Diameter.*—Apex: 1 mm. Base: 0.5 mm.

*Length.*—4 mm.

*Quantity per inflorescence.*—Approximately 100.

*Androecium.*—Presence: Present only on disc florets. Stamen quantity per floret : 5. Anther length: About 1 mm. Anther shape: Oval. Anther color: 17A.

*Pollen color.*—17A.

*Amount of pollen.*—Very small.

*Gynoecium.*—Presence: Present on ray and disc florets. Pistil number per floret: 1. Pistil length: Approximately 3 mm. Style color: 144D. Style length: Approximately 1 mm. Stigma color: 14A. Stigma shape: Bilobed. Ovary color: 144C.

Seed and fruit development: Seed and fruit development has not been observed to date.

Disease resistance: No disease/pest resistance has been observed to date.

Temperature/weather tolerance: Plants of the new *Argyranthemum* have been observed to be tolerant to rain, wind and to temperatures from 0° C. to 36° C.

What is claimed is:

1. A new and distinct variety of *Argyranthemum frutescens* plant, named 'Argymip,' as substantially illustrated and described herein.

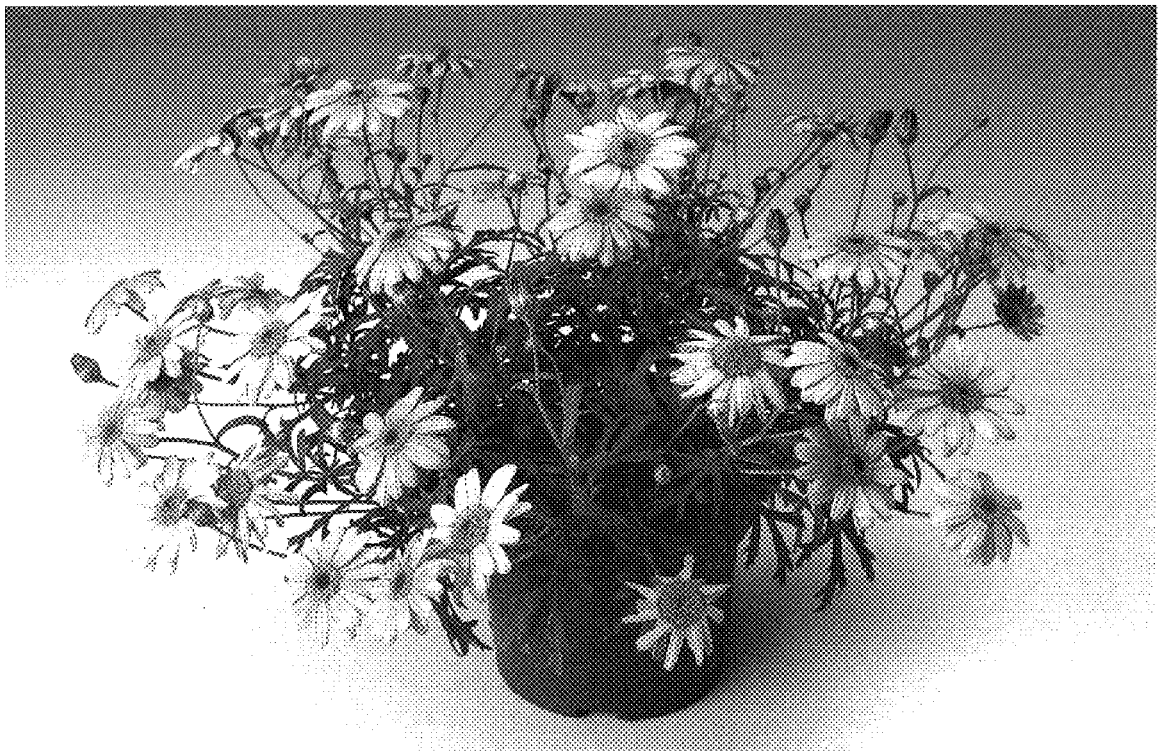

* * * * *